(12) United States Patent
Lisogurski (10) Patent No.: US 8,731,649 B2
(45) Date of Patent: May 20, 2014

(54) SYSTEMS AND METHODS FOR ANALYZING CHANGES IN CARDIAC OUTPUT

(75) Inventor: Dan Lisogurski, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/598,839

(22) Filed: Aug. 30, 2012

(65) Prior Publication Data

US 2014/0066797 A1    Mar. 6, 2014

(51) Int. Cl.
*A61B 5/0402* (2006.01)

(52) U.S. Cl.
USPC .......................................................... 600/516

(58) Field of Classification Search
USPC .................... 600/508, 512, 516, 517, 526
See application file for complete search history.

(56) References Cited

U.S. PATENT DOCUMENTS

| | | | |
|---|---|---|---|
| 4,094,308 A | 6/1978 | Cormier | |
| 4,282,655 A | 8/1981 | Tinman | |
| 4,289,141 A | 9/1981 | Cormier | |
| 4,450,527 A | 5/1984 | Sramek | |
| 5,025,795 A * | 6/1991 | Kunig | 600/526 |
| 5,092,339 A | 3/1992 | Geddes | |
| 5,178,151 A | 1/1993 | Sackner | |
| 5,275,159 A | 1/1994 | Griebel | |
| 5,331,960 A | 7/1994 | Krenzke | |
| 5,408,327 A | 4/1995 | Geiler | |
| 5,458,116 A * | 10/1995 | Egler | 600/523 |
| 5,595,182 A | 1/1997 | Krivitski | |
| 5,713,367 A * | 2/1998 | Arnold et al. | 600/517 |
| 5,743,268 A | 4/1998 | Kabal | |
| 5,817,010 A | 10/1998 | Hibl | |
| 5,833,618 A | 11/1998 | Caro | |
| 5,913,826 A | 6/1999 | Blank | |
| 5,935,066 A | 8/1999 | Harris | |
| 6,004,272 A | 12/1999 | Barry | |
| 6,045,509 A | 4/2000 | Caro | |
| 6,155,984 A | 12/2000 | Krivitski | |
| 6,292,686 B1 | 9/2001 | Chaiken | |
| 6,371,921 B1 | 4/2002 | Caro | |
| 6,389,306 B1 | 5/2002 | Chaiken | |

(Continued)

FOREIGN PATENT DOCUMENTS

| | | |
|---|---|---|
| EP | 0 537 383 | 4/1993 |
| EP | 0 841 034 | 5/1998 |

(Continued)

OTHER PUBLICATIONS

"Why measure resting heart rate?" Nauman (2012).

(Continued)

*Primary Examiner* — Brian T Gedeon
(74) *Attorney, Agent, or Firm* — Joseph M. Butscher; The Small Patent Law Group, LLC (57) ABSTRACT

A system is provided including a cardiac output monitor configured to be operatively connected to a detection module that obtains electrocardiogram (ECG) signals from the patient. The monitor includes an axis analysis module and a cardiac output module. The axis analysis module is configured to obtain ECG axis information including information corresponding to at least one ECG axis of a patient. The axis analysis module is also configured to determine ECG axis change information corresponding to a change in the ECG axis information of the patient. The cardiac output analysis module is configured to determine a change in cardiac output using the ECG axis change information.

29 Claims, 4 Drawing Sheets

(56) References Cited

U.S. PATENT DOCUMENTS

| | | |
|---|---|---|
| 6,503,206 B1 | 1/2003 | Li |
| 6,616,613 B1 | 9/2003 | Goodman |
| 6,719,705 B2 | 4/2004 | Mills |
| 6,740,072 B2 | 5/2004 | Starkweather |
| 6,754,523 B2 | 6/2004 | Toole |
| 6,758,822 B2 | 7/2004 | Romano |
| 6,760,608 B2 | 7/2004 | Lynn |
| 6,776,764 B2 | 8/2004 | Pinsky |
| 6,816,266 B2 | 11/2004 | Varshneya |
| 6,869,402 B2 | 3/2005 | Arnold |
| 6,875,176 B2 | 4/2005 | Mourad |
| 7,022,077 B2 | 4/2006 | Mourad |
| 7,033,320 B2 | 4/2006 | Von Behren |
| 7,054,679 B2 * | 5/2006 | Hirsh ............................ 600/523 |
| 7,056,292 B2 | 6/2006 | Hutchinson |
| 7,171,271 B2 | 1/2007 | Koh |
| 7,220,230 B2 | 5/2007 | Roteliuk |
| 7,452,333 B2 | 11/2008 | Roteliuk |
| 7,462,152 B2 | 12/2008 | Kolluri |
| 7,615,011 B2 | 11/2009 | Sugo |
| 7,674,231 B2 | 3/2010 | McCombie |
| 7,704,209 B2 | 4/2010 | Bennett |
| 7,747,301 B2 | 6/2010 | Cheng |
| 7,785,263 B2 | 8/2010 | Roteliuk |
| 7,806,830 B2 | 10/2010 | Bernstein |
| 7,850,617 B2 | 12/2010 | Goedje |
| 7,881,762 B2 | 2/2011 | Kling |
| 7,894,869 B2 | 2/2011 | Hoaran |
| 7,894,889 B2 * | 2/2011 | Zhang ............................ 600/512 |
| 7,899,510 B2 | 3/2011 | Hoaran |
| 7,976,472 B2 | 7/2011 | Kiani |
| 8,068,906 B2 * | 11/2011 | Chetham ........................ 600/547 |
| 8,073,516 B2 | 12/2011 | Scharf |
| 8,073,518 B2 | 12/2011 | Chin |
| 8,187,197 B2 | 5/2012 | Shapira |
| 8,211,031 B2 | 7/2012 | Poupko |
| 2002/0022785 A1 | 2/2002 | Romano |
| 2002/0082485 A1 | 6/2002 | Faithfull |
| 2003/0167012 A1 | 9/2003 | Friedman |
| 2005/0080345 A1 | 4/2005 | Finburgh |
| 2005/0085707 A1 | 4/2005 | Korsten |
| 2005/0124903 A1 | 6/2005 | Roteliuk |
| 2005/0240087 A1 | 10/2005 | Keenan |
| 2006/0184051 A1 | 8/2006 | Hempstead |
| 2006/0224053 A1 | 10/2006 | Black |
| 2007/0093702 A1 | 4/2007 | Yu |
| 2007/0213625 A1 | 9/2007 | Nayak |
| 2007/0249949 A1 | 10/2007 | Hadley |
| 2008/0082004 A1 | 4/2008 | Banet |
| 2008/0119329 A1 | 5/2008 | Punkka |
| 2008/0139958 A1 | 6/2008 | Uemura |
| 2008/0183232 A1 | 7/2008 | Voss |
| 2008/0287815 A1 | 11/2008 | Chon |
| 2009/0099459 A1 | 4/2009 | Svanberg |
| 2009/0149762 A1 | 6/2009 | Yang |
| 2009/0177110 A1 | 7/2009 | Lyden |
| 2009/0198140 A1 | 8/2009 | Aboy |
| 2009/0204012 A1 | 8/2009 | Joeken |
| 2009/0240119 A1 | 9/2009 | Schwaibold |
| 2009/0326353 A1 | 12/2009 | Watson |
| 2009/0326388 A1 | 12/2009 | Watson |
| 2009/0326395 A1 | 12/2009 | Watson |
| 2010/0016739 A1 | 1/2010 | Shelley |
| 2010/0049007 A1 | 2/2010 | Sterling |
| 2010/0049071 A1 | 2/2010 | Goor |
| 2010/0081895 A1 | 4/2010 | Zand |
| 2010/0152547 A1 | 6/2010 | Sterling |
| 2010/0152591 A1 | 6/2010 | Yu |
| 2010/0160794 A1 | 6/2010 | Banet |
| 2010/0191128 A1 | 7/2010 | Shelley |
| 2010/0210924 A1 | 8/2010 | Parthasarathy |
| 2010/0249542 A1 | 9/2010 | Thijs |
| 2010/0249559 A1 | 9/2010 | Lovejoy |
| 2010/0249612 A1 | 9/2010 | Cohen |
| 2010/0268090 A1 | 10/2010 | Rubinstein |
| 2010/0268101 A1 | 10/2010 | Sugo |
| 2010/0268518 A1 | 10/2010 | Sugo |
| 2010/0298689 A1 | 11/2010 | Wang |
| 2010/0324388 A1 | 12/2010 | Moon |
| 2010/0324431 A1 | 12/2010 | Addison |
| 2010/0324827 A1 | 12/2010 | Addison |
| 2011/0009754 A1 | 1/2011 | Wenzel |
| 2011/0009755 A1 | 1/2011 | Wenzel |
| 2011/0026784 A1 | 2/2011 | Van Slyke |
| 2011/0034813 A1 | 2/2011 | Cohen |
| 2011/0040345 A1 | 2/2011 | Wenzel |
| 2011/0060234 A1 | 3/2011 | Zhou |
| 2011/0060531 A1 | 3/2011 | Sugo |
| 2011/0077532 A1 | 3/2011 | Kim |
| 2011/0087115 A1 | 4/2011 | Sackner |
| 2011/0098112 A1 | 4/2011 | LeBoeuf |
| 2011/0098546 A1 | 4/2011 | Farazi |
| 2011/0105918 A1 | 5/2011 | Fortin |
| 2011/0172504 A1 | 7/2011 | Wegerich |
| 2011/0209915 A1 | 9/2011 | Telfort |
| 2011/0224564 A1 | 9/2011 | Moon |
| 2011/0270097 A1 | 11/2011 | Aboy |
| 2011/0301436 A1 | 12/2011 | Teixeira |
| 2012/0022350 A1 | 1/2012 | Teixeira |
| 2012/0029320 A1 | 2/2012 | Watson |
| 2012/0029361 A1 | 2/2012 | Addison |
| 2012/0029363 A1 | 2/2012 | Lund |
| 2012/0046557 A1 | 2/2012 | Kiani |
| 2012/0053433 A1 | 3/2012 | Chamoun |
| 2012/0053469 A1 | 3/2012 | Melker |
| 2012/0065485 A1 | 3/2012 | Benni |
| 2012/0065527 A1 | 3/2012 | Gill |
| 2012/0065528 A1 | 3/2012 | Gill |
| 2012/0078069 A1 | 3/2012 | Melker |
| 2012/0109018 A1 | 5/2012 | Gertner |
| 2012/0136261 A1 | 5/2012 | Sethi |
| 2012/0172723 A1 | 7/2012 | Gertner |

FOREIGN PATENT DOCUMENTS

| | | |
|---|---|---|
| EP | 1 443 856 | 2/2006 |
| EP | 1 769 737 | 4/2007 |
| EP | 1 884 189 | 2/2008 |
| EP | 2 281 508 | 2/2011 |
| EP | 2 047 794 | 2/2012 |
| EP | 2 217 140 | 2/2012 |
| WO | WO 91/13589 | 9/1991 |
| WO | WO 94/14372 | 7/1994 |
| WO | WO 97/47236 | 12/1997 |
| WO | WO 98/41279 | 9/1998 |
| WO | WO 02/03076 | 1/2002 |
| WO | WO 03/082099 | 10/2003 |
| WO | WO 2004/071292 | 8/2004 |
| WO | WO 2005/055825 | 6/2005 |
| WO | WO 2006/100676 | 9/2006 |
| WO | WO 2007/109065 | 9/2007 |
| WO | WO 2008/094598 | 8/2008 |
| WO | WO 2008/144404 | 11/2008 |
| WO | WO 2008/144525 | 11/2008 |
| WO | WO 2009/009761 | 1/2009 |
| WO | WO 2009/014420 | 1/2009 |
| WO | WO 2009/101140 | 8/2009 |
| WO | WO 2010/001231 | 1/2010 |
| WO | WO 2010/045556 | 4/2010 |
| WO | WO 2011/080190 | 7/2010 |
| WO | WO 2010/096475 | 8/2010 |
| WO | WO 2010/111073 | 9/2010 |
| WO | WO/2010/124034 | 10/2010 |
| WO | WO 2010/146326 | 12/2010 |
| WO | WO 2010/146327 | 12/2010 |
| WO | WO 2011/047211 | 4/2011 |
| WO | WO 2011/050066 | 4/2011 |
| WO | WO 2011/051822 | 5/2011 |
| WO | WO 2011/060220 | 5/2011 |
| WO | WO 2011/077294 | 6/2011 |
| WO | WO 2011/080194 | 7/2011 |
| WO | WO2011/087927 | 7/2011 |
| WO | WO 2011/089488 | 7/2011 |
| WO | WO 2012/009350 | 1/2012 |

(56) References Cited

FOREIGN PATENT DOCUMENTS

| WO | WO 2012/014065 | 2/2012 |
|---|---|---|
| WO | WO 2012/015426 | 2/2012 |
| WO | WO 2012/027613 | 3/2012 |
| WO | WO 2012/032413 | 3/2012 |
| WO | WO 2012/032536 | 3/2012 |
| WO | WO 2012/052926 | 4/2012 |
| WO | WO 2012/075322 | 6/2012 |
| WO | WO 2012/076957 | 6/2012 |

OTHER PUBLICATIONS

"The shape and dimensions of photoplethsymographic pulse waves; a measurement repeatability study," Marcinkevics, et al. Acta Universitatis Latviensis,vol. 753, Bilology, pp. 99-106 (2009).

"Monitoring of Reactive Hyperemia Using Photoplethysmographic Pulse Amplitude and Transit Time," Selvavaj, et al. Journal of Clinical Monitoring and Computing 23:315-322 (2009).

"Photoacoustic thermal diffusion flowmetry," Sheinfeld, et al., Biomedical Optics Express vol. 3, No. 4 (2012).

"Flow dependent photothermal modulation of the photacoustic response," Sheinfeld, et al, Photonos Plus Ultrasound: Imaging and Sensing (2012).

"Relation between repiratory variations in pulse oximetry plethysmographic waveform amplitude and arterial pulse pressure in ventilated patients," Cannesson, et al. Ciritical Care (2005).

"Pulse oximeter plethysmograph variation and its relationship to the arterial waveform in mechanically ventilated childer," Chandler, et al. J. Clin. Monit. Comput. (2012).

"Variations in Arterial Blood Pressure and Photoplethysmography During Mechanical Ventilation," Natalani, et al., Technology, Computing, and Simulation, vol. 103, No. 5, (2006).

"Derivation of Respiratory Signals from Multi-lead ECGS, Moody," et al. (1985).

"Photoplethsmography and its application in clinical physiological measurement," Physiol. Meas. 28 (2007).

"Venus Oximetry," Signa Vitae 2007.

"Near-Infrared Spectrometry (NIRS) and Venous-side Monitoring of the Circulation," Hoffman, Nov. 23, 2013 DOI: 10.1111/pan.12301.

"On the Analysis of Fingertip Photoplethysmogram Signals," Elgendi, Current Cardiology Reviews, 2012.

"A Computer Based Photoplethysmographic Vascular Analyzer Through Derivatives," Gonzalez, et al, Computers in Cardiology (2008).

"Noninvasive Assessment of the Digital Volume Pulse: Comparison with the Peripheral Pressure Pulse," Millasseau, et al., Journal of the American Heart Association (2000).

"Non-Invasive Estimation of Cardiac Output from Finger Photoplethysmogram Based on Windkessel Model," Poon, Bulletin of Advance Technology Research, vol. 4, No. 6 (2010).

"Non-constrained Blood Pressure Monitoring Using ECG and PPG for Personal Healthcare," Yoon, et al, (2008).

"How to measure heart rate?" Vogel, et al. Eur. J. Clin Paramacol (2004) 60.461-466.

"Resting Heart Rate in Cardiovascular Disease," Fox, et al. Journal of the Amercan College of Cardiology vol. 50, No. 9 (2007).

* cited by examiner

SYSTEMS AND METHODS FOR ANALYZING CHANGES IN CARDIAC OUTPUT

FIELD

Embodiments of the present disclosure generally relate to physiological signal processing, and more particularly, to processing signals to analyze changes in cardiac output of a patient.

BACKGROUND

Cardiac output is the volume of blood pumped by the heart. Cardiac output may be divided by body surface area to account for the size of a patient.

Cardiac output may be used to assess the state of a patient's circulation. Simple measurements, such as heart rate and/or blood pressure, may be adequate to understand cardiac output for some patients, but more detailed measurements may be required, for example, in the event of any cardiovascular abnormality. Hypotension or low blood pressure may occur in a wide range of patients (for example, due to low cardiac output), especially those in intensive care or postoperative high dependency units. Measurement of cardiac output may be useful to establish a patient's initial cardiovascular state or to measure the patient's response to various therapeutic interventions. However, current methods of measuring cardiac output suffer from a variety of drawbacks. For example, arterial catheters used in measuring cardiac output are highly invasive. As another example, collection of exhaled gases may be used to measure cardiac output, but accurate collection may be difficult due to leaks around a facemask or mouthpiece.

SUMMARY

Certain embodiments of the present disclosure provide a system that may include a cardiac output monitor configured to be operably connected to a detection module that obtains electrocardiogram (ECG) signals from the patient. The monitor includes an axis analysis module and a cardiac output module. The axis analysis module may be configured to obtain ECG axis information including information corresponding to at least one ECG axis of a patient. The axis analysis module may be configured to determine ECG axis change information corresponding to a change in the ECG axis information of the patient. The cardiac output analysis module may be configured to determine a change in cardiac output using the ECG axis change information.

The ECG axis information may include first axis information corresponding to a first axis corresponding to a first portion of a cardiac cycle, second axis information corresponding to a second axis corresponding to a second portion of the cardiac cycle, and difference information corresponding to a computed value derived from the first axis information and the second axis information. Further, the ECG axis change information may include information describing a change in the difference information over time. For example, the first axis may correspond to at least one of a P wave, Q wave, R wave, or S wave, and the second axis may correspond to a T wave.

In some embodiments, the ECG axis information may include information corresponding to a multi-planar ECG axis.

The cardiac output monitor may be configured to adjust the ECG axis change information to account for a respiratory effect.

In some embodiments, the cardiac output monitor may be configured to identify a predetermined number of breathing cycles, to collect a first set of the ECG axis information over a first group of breathing cycles, to collect a second set of the ECG axis information over a second group of breathing cycles, and to determine the ECG axis change information using a difference between the first set of the ECG axis information and the second set of the ECG axis information. The first set and the second set of the ECG axis information may each be collected for the predetermined number of breathing cycles.

Certain embodiments provide a method for determining changes in cardiac output. The method includes obtaining electrocardiogram (ECG) axis information of the patient. The ECG axis information may be based on information obtained from a detection module operatively connected to the patient. The method may also include determining a change in the ECG axis information over time. Further, the method may include determining, at a processing unit, a change in cardiac output based on the change in the ECG axis information.

Certain embodiments provide a tangible and non-transitory computer readable medium including one or more computer software modules. The one or more computer software modules are configured to direct a processor to obtain electrocardiogram (ECG) axis information of a patient based on information obtained from a detection module operatively connected to the patient. Also, the one or more computer software modules are configured to direct a processor to determine a change in the ECG axis information over time. Further, the one or more computer software modules are configured to direct a processor to determine a change in cardiac output based on the change in the ECG axis information.

Embodiments provide for the determination of changes in cardiac output using non-invasive techniques, such as electrodes used to obtain ECG information including, for example, ECG axis information. Also, embodiments provide for non-invasive determination of changes in cardiac output using equipment, such as ECG sensors, that are readily available and used with many patients, thereby avoiding or reducing the use of additional detection equipment. Thus, embodiments provide for reduced cost of cardiac output determination as well as reduced clutter in the area surrounding a patient and/or reduced numbers of sensors that must be attached to a patient.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

DETAILED DESCRIPTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Embodiments of the present disclosure provide for non-invasive determination of cardiac output using readily available sensing components frequently attached to a patient for conventional monitoring techniques. Thus, for example, embodiments of the present disclosure provide for cardiac output determination using relatively inexpensive and convenient sensing or detection techniques, as the expense and inconvenience of additional sensing or detecting equipment is avoided or reduced. Embodiments of the present disclosure track changes in heart position using ECG axis information, and track changes in cardiac output based on changes in the ECG axis information over time.

Figure 1:
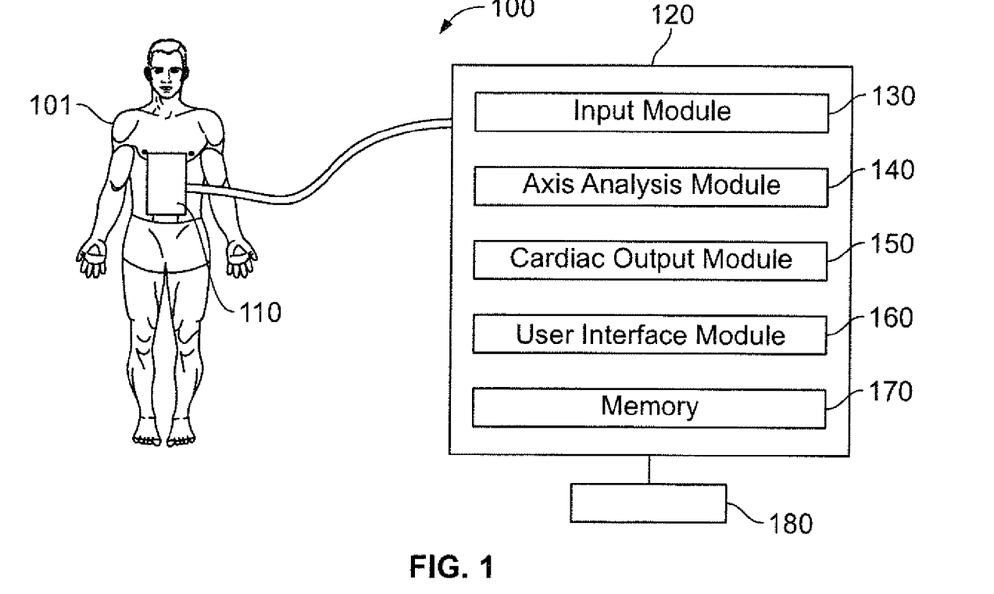
FIG. 1 illustrates a schematic diagram of a system for analyzing cardiac output according to an embodiment.

FIG. 1 illustrates a schematic diagram of a system 100 for analyzing cardiac output according to an embodiment. The system 100 may be used in conjunction with embodiments or aspects of methods and systems described elsewhere herein. The system 100 includes a detection module 110 and a cardiac output monitor 120. The detection module 110 is intended as a schematic representation. In some embodiments, the detection module 110 may include a standard set of ECG electrodes, such as the 10 electrodes typically used in a 12-lead ECG system. In the illustrated embodiment, the cardiac output monitor 120 is configured to determine a change in cardiac output using information provided by the detection module 110. In the embodiment illustrated in FIG. 1, a patient 101 is shown being monitored by the system 100.

The various systems, modules, monitors and units disclosed herein may include a controller, such as a computer processor or other logic-based device that performs operations based on one or more sets of instructions (e.g., software). The instructions on which the controller operates may be stored on a tangible and non-transitory (e.g., not a transient signal) computer readable storage medium, such as a memory. The memory may include one or more computer hard drives, flash memory, RAM, ROM, EEPROM, and the like. Alternatively, one or more of the sets of instructions that direct operations of the controller may be hard-wired into the logic of the controller, such as by being hard-wired logic formed in the hardware of the controller.

The detection module 110 is configured to sense one or more outputs or characteristics of the cardiovascular activity of the patient 101 from which a cardiovascular axis may be constructed. The system 100 may be configured to utilize changes in ECG axis information to analyze changes in cardiac output. The detection module 110 thus may include sensors configured to provide ECG information. For example, the detection module 110 may include a plurality of electrodes configured to be positioned on the patient 101, via adhesive pads (see, e.g. FIG. 6 and related discussion). The detection module 110 may include a 4-lead ECG detection configuration. In other embodiments, the detection module 110 may include a 12-lead ECG detection configuration, a 15-lead ECG detection configuration, an 18-lead ECG detection configuration, or any other electrode configuration suitable for determining an ECG axis. For example, in some embodiments, a system using 5 electrodes to estimate a 12-lead ECG may be used.

In some embodiments, the detection module 110 may also include a processor or monitor configured to process information collected by, for example, ECG electrodes. The processing may include, for example, removal of noise or other artifacts from signals collected by the ECG electrodes, and/or construction of one or more ECG waveforms representative of the cardiac cycle of the patient. The detection module 110 may further include a display for displaying information, such as one or more ECG waveforms, to a practitioner. In some embodiments, the detection module 110 provides information in a raw state to the cardiac output monitor 120. In other embodiments, the detection module 110 first processes information collected by the ECG electrodes (e.g. removes noise and/or other artifacts, and/or develops one or more waveforms and/or axes), and communicates the processed information to the cardiac output monitor.

Figure 2:
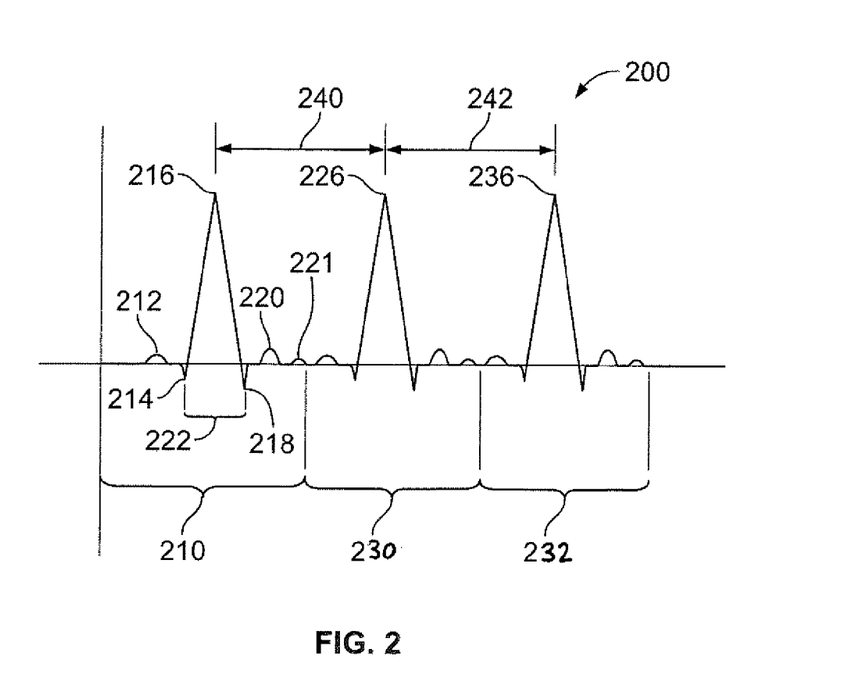
FIG. 2 illustrates an electrocardiogram (ECG) signal according to an embodiment.

FIG. 2 illustrates an ECG signal 200 according to an embodiment. The ECG signal 200 is representative of cardiac activity of a patient. The depicted ECG signal 200 represents a plurality of cardiac cycles including a first cardiac cycle 210, a second cardiac cycle 230, and a third cardiac cycle 232. In the illustrated embodiment, the depicted cardiac rhythm is substantially uniform, with each of the cardiac cycles 210, 230, and 232 substantially similar to each other, so that a description of the first cardiac cycle 210 will suffice for an understanding of the cardiac cycles 210, 230, and 232.

The first cardiac cycle 210 includes a P-wave 212, a Q-wave 214, an R-wave 216, an S-wave 218, a T-wave 220, and a U-wave 221. The P-wave, which generally appears as a relatively small positive deflection of the ECG signal 200, corresponds to the depolarization of the atria (the smaller chambers of the heart), when the atria depolarize to pump blood into the ventricles (the larger chambers of the heart).

The QRS complex 222 (which includes the Q-wave 214, the R-wave 216, and the S-wave 218) corresponds generally to the depolarization of the ventricles just before the muscle contracts and ejects blood from the heart into the aorta and pulmonary artery. Together, the Q-wave 214, R-wave 216, and S-wave 218 form the QRS complex 222. The Q-wave 214 generally appears as a relatively small negative deflection of the ECG signal 200, followed by the R-wave 216 which appears generally as a relatively large positive deflection of the ECG signal 200. The R-wave 216 is followed by the S-wave 218, which generally appears as a relatively small negative deflection of the ECG signal 200.

After the ventricles depolarize to pump blood from the heart to the rest of the body, the ventricles re-polarize. The re-polarization of the ventricles corresponds to the T-wave 220 of the ECG signal 200. The T-wave 220 generally appears as a relatively small positive deflection of the ECG signal 200. The U-wave 221 may be visible for some subjects and correspond to the repolarization of the Purkinje fibers.

The second cardiac cycle 230 includes an R-wave 226, and the third cardiac 232 cycle includes an R-wave 236. The distance 240 from the peak of the R-wave 226 of the second cardiac cycle 230 to the peak of the R-wave 216 of the first cardiac cycle 210 (the difference between an R-wave of a first cycle and an R-wave of an immediately following cycle may be referred to as an R-R interval) may be used to define the period between the first cardiac cycle 210 and the second cardiac cycle 230. Similarly, the distance 242 from the peak of the R-wave 236 of the third cardiac cycle 232 to the peak of the R-wave 226 of the second cardiac cycle 230 may be used to define the period between the second cardiac cycle 230 and the third cardiac cycle 232. One or more R-R intervals may be used to determine the heart rate of a patient.

Returning to FIG. 1, the cardiac output monitor 120 is configured to receive information from the detection module 110 (e.g. information describing the ECG of the patient 101), analyze changes in one or more ECG axes defined by the received ECG information, and to analyze changes in the cardiac output of the patient 101 using the changes in one or more ECG axes. The cardiac output monitor 120 includes an input module 130, an axis analysis module 140, a cardiac output module 150, a user interface module 160, a memory 170, and a display 180.

In the illustrated embodiment, the cardiac output monitor 120 is depicted as a stand-alone unit including various modules, such as an axis analysis module 140, a cardiac output module 150, and a display module 180. In some embodiments, all or a portion of the cardiac output monitor 120 may be incorporated into other components, such as an ECG monitor, telemetry unit, or, as another example, a multi-parameter medical monitor. In some embodiments, one or more modules of the cardiac output monitor 120 may be shared with one or more other components or aspects of a medical monitoring system. For example, the cardiac output monitor 120 may share a display unit with another component, such as an ECG monitor or a multi-parameter medical monitor.

The input module 130 of the cardiac output monitor 120 is configured to receive information from the detection module 110. The information received from the detection module 110 may be raw (e.g., as detected by one or more sensors) or processed (e.g., by removing noise or other artifacts, and/or by constructing a waveform using the information detected by the sensors). The input module 130 or the detection module 110 may be configured to combine information from individual electrodes to generate standard or non-standard electrical vectors (e.g., Lead I, II, II, aVR, aVL, aVF, V1-V6, etc.) For example, in embodiments in which the input module 130 receives raw information directly from the sensors of the detection module, the input module 130 may construct one or more ECG waveforms representative of the cardiac activity of the patient 101 using the detected information. Further, for example, in some embodiments, the input module may construct one or more ECG axes for each cardiac cycle in a group of cardiac cycles to be analyzed.

In some embodiments, a QRS axis corresponding to the orientation of the ECG axis during one or more QRS complexes is constructed using ECG information from the detection module 110. Additionally or alternatively, a T axis may be constructed corresponding to the orientation of the ECG axis during one or more T waves. As another example, a P axis may be constructed corresponding to the orientation of the ECG axis during one or more P waves. Further still, additionally or alternatively to a QRS axis, separate axes may be constructed corresponding to one or more of the Q wave, the R wave, or the S wave. In some embodiments, the axis analysis module determines one or more axes for each cardiac cycle of a given sample. In some embodiments, the axis analysis module determines an average axis for a given number of cycles. For example, at a first time interval, about 60 seconds of ECG information may be obtained.

The axis analysis module 140 may compute an average QRS axis using a QRS axis from each cycle occurring during the first time interval, and compute an average T axis using a T axis from each cycle occurring during the first time interval. At a second time interval, for example, about an hour later than the first time interval, about 60 seconds of ECG information may be obtained. The axis analysis module 140 may again compute an average QRS axis using a QRS axis from each cycle occurring during the second time interval, and compute an average T axis using a T axis from each cycle occurring during the second time interval. The axis analysis module 140 may then determine changes regarding the axes from the first time period to the second time period, and communicate information regarding the determined changes from the first time period to the second time period to the cardiac output module 150.

Figure 3:
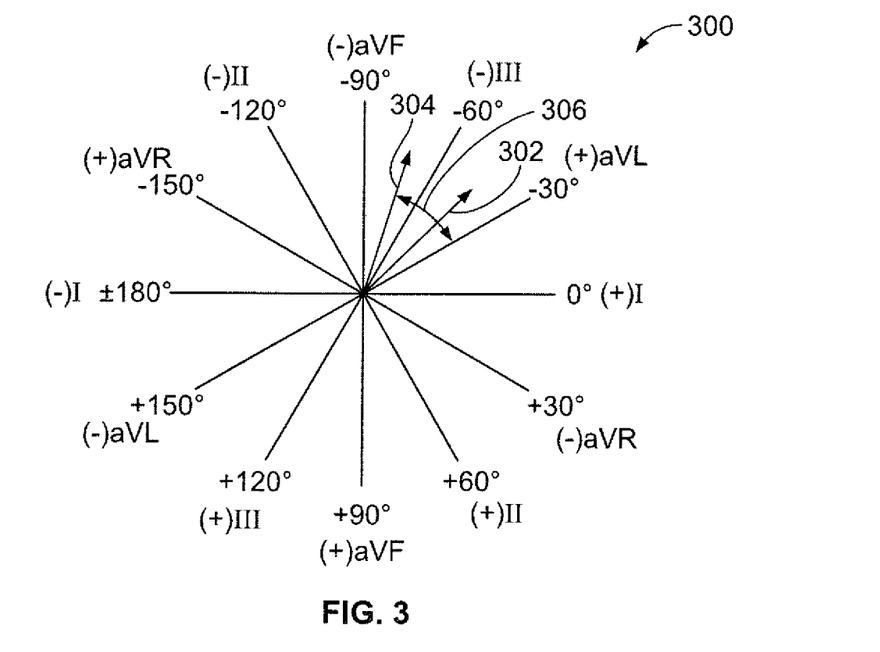
FIG. 3 illustrates an ECG axis diagram according to an embodiment.

FIG. 3 illustrates an ECG axis diagram 300 according to an embodiment. An ECG axis may be understood as a vector describing the motion of a de-polarization wave of a heart, and may be obtained using ECG information from a plurality of leads recording cardiac activity from different angles. The ECG axis diagram 300 represents a frontal plane axis diagram corresponding to a frontal plane of a patient. In other embodiments, a different plane may be used, or a multi-planar (e.g. 3 dimensional) analysis may be employed (see, e.g. FIG. 5 and related discussion). Two axes are depicted in FIG. 3, namely, a QRS axis 302 and a T axis 304. The QRS axis 302 corresponds to the ECG axis for the QRS complex of a given cycle (e.g., QRS complex 222), and the T axis 304 corresponds to the ECG axis for the T wave from the same cycle (e.g., T wave 220). In some embodiments, the QRS axis 302 may represent an average QRS axis for a given number of QRS cycles or over a given time period, and the T axis 304 may represent a corresponding average T axis over the same number of cycles or over the same given time period.

The ECG axis diagram 300 corresponds to a frontal plane as determined using the first 6 leads of a standard 12 lead system. (See also FIG. 6 and related discussion.) These leads are identified as the I, II, III, aVL, aVR, and aVF leads on the ECG axis diagram 300. The positive and negative portions of each lead are at 180 degrees to each other and define an axis. Each axis depicted on the ECG axis diagram extends between a positive and a negative of a given lead. For example, an axis extending from −30 degrees to +150 degrees corresponds to the positive and negative portions of the aVL lead. As the ECG axis diagram 300 thus includes six axes (one axes for each lead), the ECG axis diagram 300 may be referred to as employing a hexaxial reference system.

The QRS axis 302 and T axis 304 may be computed or otherwise determined using information received from the detection module using conventionally known methods for determining the axes. For example, to determine the QRS axis 302, in a system having multiple leads used to detect cardiac signals, an isoelectric lead may be determined. The isoelectric lead may be defined as a lead experiencing equal forces in the positive and negative direction, and often is the lead with the smallest QRS amplitude. The QRS axis 302 then may be defined as being perpendicular to the isoelectric lead orientation. As there are two axes or corresponding leads that are perpendicular to the isoelectric lead (one in a positive direction and one in a negative direction), the perpendicular axis that best fits the direction of the other ECG leads of the multi-lead system is chosen. For example, if the perpendicular lead is positively deflected on the ECG, then the positive direction is selected. For example, if the isoelectric lead is the I lead (e.g. the lead corresponding to the 0 degrees to 180 degrees direction), then the perpendicular lead corresponding to the I lead is the aVF lead (e.g., the lead corresponding to the +90 degrees to −90 degrees direction). If the ECG obtained by the aVF lead is positive, then the QRS axis is oriented at about +90 degrees. If a single isoelectric lead cannot be identified, generally there will be two leads that are about 30 degrees apart, and an approximate QRS axis may be selected within the 30 degree range of the respective perpendiculars. The above description of axis determination is meant solely by way of example, and in other embodiments, different techniques may be employed to identify various ECG axes. For example, the variations in the ECG axes due to cardiac output may be sufficiently small that more precise estimates of ECG axis position may be desirable. Thus, in some embodiments, conventional algorithms providing improved accuracy may be employed.

For regular cardiac rhythms of typical patients, the various axes corresponding to different portions of the cardiac cycle typically lie within known ranges. For example, a QRS axis may be considered normal if the QRS axis is oriented between about −30 degrees and about +90 degrees for the hexaxial reference system used in FIG. 3. A left axis deviation is characterized by a QRS axis oriented between about −30 degrees to about −90 degrees, and a right axis deviation is characterized by a QRS axis between about +90 degrees to about +180 degrees. A normal p wave axis typically is between about 0 degrees to about 75 degrees. Further, for example, a T wave axis may be considered normal if the difference between the T wave axis and the QRS axis is less than about 45 degrees in the frontal plane as depicted in FIG. 3.

In the embodiment depicted in FIG. 3, the QRS axis 302 is at about −45 degrees, and the T axis 304 is at about −75 degrees. Further, a difference 306 between the QRS axis 302 and the T axis 304 in the illustrated embodiment is about 30 degrees. Thus, ECG information determined or otherwise obtained by the axis analysis module may include one or more of the orientation of one or more axes for a given cardiac cycle, the average orientation for one or more axes for a given number or duration of cardiac cycles, or difference information describing a difference between a first axis for one portion of a cardiac cycle (or group of cycles) and a second axis for a distinct portion of the cardiac cycle (or group of cycles). The difference information in some embodiments may include differences for each cycle of a given number or durations of cardiac cycles. In some embodiments, the difference information may include an average difference between axes corresponding to different portions of the cardiac cycle over a given number or duration of cycles.

The axis analysis module 140 of the cardiac output monitor 120 of the illustrated embodiment is further configured to determine ECG axis change information. For example, in some embodiments, the change information may include a change from a portion of a first cycle (or group of cycles) at a first time and a corresponding portion in a second cycle (or group of cycles) at a subsequent second time. As another example, the axis information may correspond to a difference between a first portion of a cycle and a second portion of the cycle, and the change information may include information corresponding to a change in the difference information from a first cycle (or group of cycles) at a first time and a second cycle (or group of cycles) at a subsequent second time.

Figure 4:
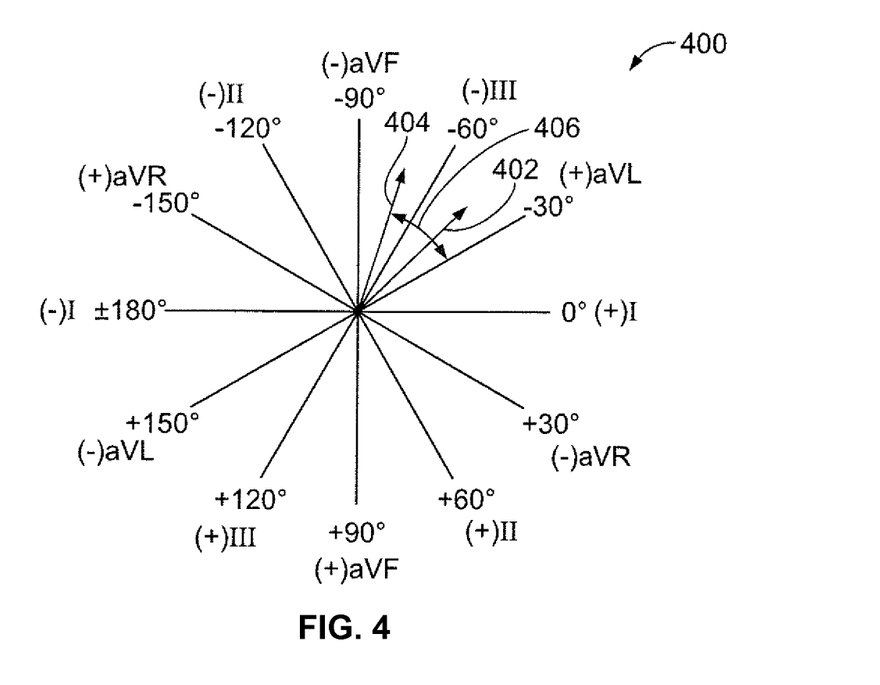
FIG. 4 illustrates an additional ECG axis diagram taken at a subsequent time according to an embodiment.

FIG. 4, in conjunction with FIG. 3 illustrates variations in ECG axes according to an embodiment. FIG. 4 depicts an ECG axis diagram 400 corresponding to an ECG cycle at a time subsequent to the ECG axis diagram 300 of FIG. 3. For example, the ECG axis diagram 300 of FIG. 3 may depict ECG information describing the cardiac activity of a patient taken at a time of $t_0$, and the ECG axis diagram 400 may depict ECG information describing the cardiac activity of a patient taken at a time about one hour later than $t_0$. The axis diagram 400 includes a QRS axis 402 corresponding to the ECG axis during the QRS complex of a cardiac cycle, a T axis 404 corresponding to the ECG axis during the T wave of the cardiac cycle, and a difference 406 representing the difference between the T axis 404 and the QRS axis 402. In some embodiments, the T axis 404 and the QRS axis 402 correspond to average axes for a given number of cardiac cycles or a given time duration.

In the embodiment depicted in FIG. 4, the QRS axis 402 is at about −50 degrees, and the T axis 404 is at about −70 degrees. Further, a difference 406 between the QRS axis 402 and the T axis 404 in the illustrated embodiment is about 20 degrees. Thus, the QRS axis 402 has changed about −5 degrees from the QRS axis 302, and the T axis 404 has changed about +5 degrees from the taxis 304. Further the difference 406 is about ten degrees less than the difference 306. The various angles and differences depicted in FIG. 4 are meant by way of example, as different angles and differences, for example, smaller differences between axes at various times, may be encountered.

In some embodiments, cardiac output may be understood as the product of average heart rate multiplied by average stroke volume. The stroke volume may be understood as the quantity of blood ejected from the heart, and is equal to end systolic volume (e.g., the blood remaining in heart after contraction) subtracted from end diastolic volume (e.g., the blood in the heart at the end of filling). With the R-R interval varying slightly over time, as well as the stroke volume varying slightly over time, the cardiac output may be computed beat by beat by summing the stroke volume from each beat over a period of time (e.g., about one minute) to determine a cardiac output in Liters per minute. The orientation (e.g, size, position) of the heart in the chest before contraction is related to the quantity of blood in the heart before contraction. Since the P and the QRS axis occur before blood is ejected, one or both axes may provide an indicator of the heart's orientation before contraction. Since the T wave occurs during repolarization, after blood has been ejected from the heart, the T axis may be an indicator of the orientation of the heart after ejection of blood from the heart. Thus, each beat may be clearly identified from a QRS complex on an ECG, and the volume of blood ejected from the heart may correspond to changes in the orientation of axes determined at particular portions of the cardiac cycle. Thus, in some embodiments, at least one axis-based indicator of end diastolic volume (e.g., P axis or QRS axis) and at least one measure of end systolic volume (e.g., T axis or U axis) may be used to track changes in cardiac output.

The change in the differences between axes may be correlated to changes in the position or volume of the heart that indicate changes in cardiac output. For example, as discussed above in connection with FIG. 2, the QRS complex of an ECG waveform corresponds to the electrical depolarization of the ventricles, and the T wave corresponds to the repolarization of the ventricles. Cardiac output may be represented by the following: CO=HR×SV, where CO is the cardiac output, HR is the heart rate, and SV is the stroke volume. Further, the SV may be defined as the end diastolic volume minus the end systolic volume.

The end of the diastolic portion of the heart beat corresponds to the QRS complex, and the end of the systolic portion of the heart beat corresponds to the T wave. As blood is pumped through the heart, the heart expands and contracts, with the filling and emptying of the heart resulting in a change in the position of the heart, and a change in the orientation of the ECG axis.

Volumetric changes of the heart thus may affect the position of the heart (and the orientation of the ECG axes at various portions of the cardiac cycle with respect to other portions of the cardiac cycle). Thus, the change in the position of the heart from the end of the diastolic portion, as represented by the QRS axis, to the end of the systolic portion, as represented by the T wave axis, may provide information regarding relative changes in cardiac output. For example, if the change in position between the QRS and T axes is larger at a first time (e.g. about 30 degrees in FIG. 3) and smaller at a second time (e.g. about 20 degrees in FIG. 4), then, because the axes are less spaced apart at the second time, the cardiac output may be understood as decreasing from the first time to the second time (if the heart rate is substantially the same at the first and second times). (It should be noted that changes in position encountered in practice may be smaller than depicted in the above example.) Thus, in some embodiments, the difference information obtained corresponds to differences between the QRS axis and the T axis (e.g., differences 306 and 406), and the change information corresponds to a change in the difference from a first cardiac cycle (or cycles) to a second cardiac cycle (or cycles). For example, the second difference (e.g., 406) may be subtracted from the first difference (e.g., 306).

In other embodiments, other axes or differences between axes may be considered, additionally or alternatively to the QRS and T axes. For example, a difference between an axis corresponding to only a portion of the QRS complex (e.g. a Q axis, R axis, or S axis) and the T axis may be considered. As another example, a difference between a P axis and one or more of the Q axis, R axis, S axis, or T axis may be considered. Still further additionally or alternatively, the change information may include information corresponding to a change from an ECG axis (or average of a number of ECG axes) at a first time to the same axis at a second time. For example, a QRS axis may be determined at a first time, a second QRS axis determined at a second time, and the change from the QRS axis at the first time to the second time included with the change information determined by the axis analysis module 140.

In some embodiments, instead of subtracting one axis from a different axis, one or more axes may be subtracted from a previous value. For example, at a time $t_0$, an average QRS axis may be represented as X, and an average T axis may be represented as Y. At a time $t_1$ (taken, for example, several minutes after $t_0$), the QRS axis may be represented as X−ΔQRS, and the T axis may be represented as Y−ΔT. Then, for example, an average change in stroke volume may be computed as being equal to f((X−(X−ΔQRS)), ((Y−(Y−ΔT))), or, in a simplified form, f(ΔQRS, ΔT), where f is an empirically determined function. For example, the function may simply subtract ΔQRS and ΔT, and use a lookup table based on calibration data from routine experimentation on human subjects who are also monitored by a more invasive form of cardiac output. In other embodiments, the function may be more complex.

Figures 5, 6:
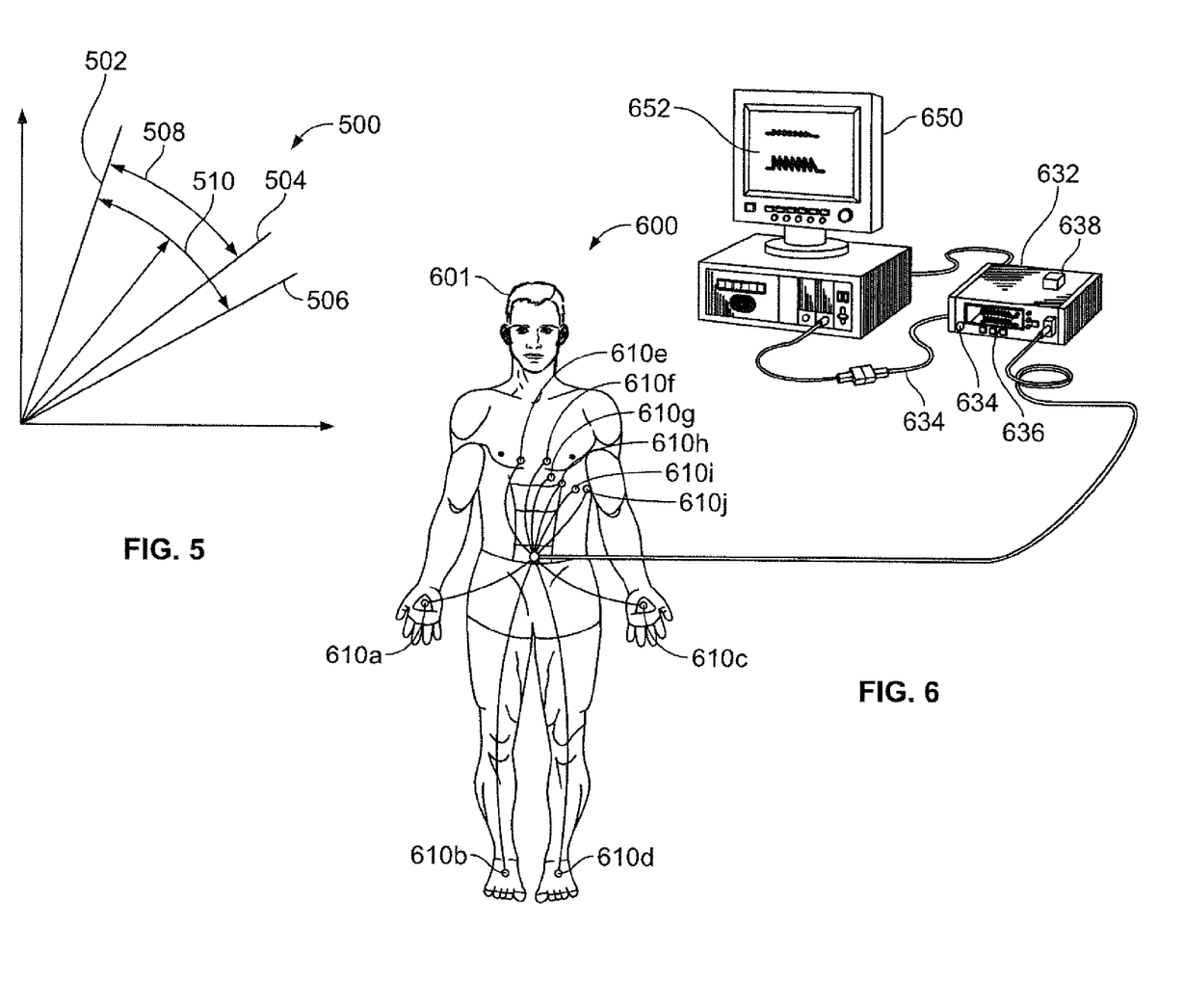
FIG. 5 illustrates variations in multiplanar ECG axes according to an embodiment.
FIG. 6 illustrates an isometric view of an ECG monitoring system according to an embodiment.

FIG. 5 illustrates variations in multiplanar ECG axes according to an embodiment. FIG. 5 depicts a three dimensional ECG axis diagram 500. The axis diagram 500 includes a QRS axis 502, a first T axis 504 and a second T axis 506. The axis diagram 500 also includes a first difference 508 between the QRS axis 502 and the first T axis 504, and a second difference 510 between the QRS axis 502 and the second T axis 506. In the illustrated embodiment, the second difference 510 is larger than the first difference 508. The various axes and differences are depicted as extending through a three dimensional space. In alternate embodiments, the axes and differences may be presented as projections along the respective axes and analyzed as coordinate components (e.g., x, y, and z components) of the depicted axes, for example.

In the embodiment depicted in FIG. 5, the first T axis 504 corresponds to a T axis for a cardiac cycle occurring at a first time, and the second T axis 506 corresponds to a T axis for a subsequent, later cardiac cycle. In the illustrated embodiment, the QRS axis 502 corresponds to the QRS axis at both the first and second times. Thus, in the illustrated embodiment, the QRS axis has not changed as measured at the first and second times. In alternate embodiments, the axes depicted in FIG. 5, for example, may represent average axes over a given time period or number of cardiac cycles.

The embodiment depicted in FIG. 5 presents an example of increased cardiac output between the first and second time (assuming generally constant heart rate). For example, after the first time at which the QRS axis 502 and the first T axis 504 were obtained, a patient may receive a treatment that results in a higher ejection fraction. Thus, at the subsequent second time, the stroke volume may have increased and the heart may be contracting more from a position corresponding to the QRS axis to a position corresponding to the T axis, without substantially affecting the position corresponding to the QRS axis. Thus, in FIG. 5, the QRS axis 502 is depicted as stationary (e.g. a single QRS axis for both times), while the T axes 504, 506, are distinct (with the second T axis 506 being a greater difference 510 away from the QRS axis 502 than the difference 508 between the first T axis 504 and the QRS axis 502).

In some embodiments, the axis analysis module 140 may also be configured to adjust for respiratory effects. For example, the movement of the chest of a patient during breathing may also affect the position of the heart, resulting in a change in one or more axes due to respiration. Thus, movement due to respiration may confound the determination of movement of one or more axes due to volumetric changes of the heart. In some embodiments, the axis analysis module 140 (or other aspect of the cardiac output monitor 120) identifies and/or accounts for effects of respiration.

For example, respiratory information corresponding to movement of ECG axes due to respiration may be obtained by examining ECG cycles using conventional techniques. The respiratory information may include information corresponding to the beginning, ending, and/or number of respiratory cycles for a given sample, or may include information corresponding to the amount of a change in one or more axes due to movement of the chest caused by breathing. The change in position due to the respiration may be subtracted from the total change in position (for example, for each cycle) to provide a net change of position removing the effects of respiration. For example, with reference to FIGS. 3 and 4, if it is determined that a respiration effect was responsible for about 5 degrees of the change between the first time (e.g. the time at which the axes of FIG. 3 were obtained) and the second time (e.g. the time at which the axes of FIG. 4 were obtained), then the change information may be adjusted to account for the about 5 degree change due to respiration (e.g. about 5 degrees added to or subtracted from the determined total change in the differences of the axes, as appropriate).

The axis analysis module 140 may be configured to obtain respiratory information from devices other than the detection module 110. For example, information corresponding to inspiration phase, expiration phase, an inspiration to expiration ratio, or other respiratory information may be obtained from a variety of devices, including a ventilator, a respiration band, nasal thermistor, $EtCO_2$ monitor, or the like. Further, in some embodiments, respiratory information may be obtained from an analysis of a photoplethysmograph (PPG), or as another example, from transthoracic bioimpedance information.

In other embodiments, the effects of respiration may be effectively averaged away. For example, in some embodiments, ECG information is analyzed to determine the presence and number of respiratory cycles for a given sample collection. For example, a first time period of ECG axes may be collected during a predetermined number of respiratory cycles, for example, about 15. Then, at a second time, for example, about an hour later than the first time period, a second time period of ECG axes may be collected during the same predetermined number of respiratory cycles. In still other embodiments, the ECG information may be collected for time periods selected to be sufficiently long to contain a sufficient number of respiratory cycles to allow averaging out of the effects of respiration. For example, in some embodiments, ECG information is obtained for a first time duration of about one minute, and later obtained for a second time duration of about one minute occurring about one hour later. Thus, changes in cardiac output may be examined on an hourly basis. Other intervals, either shorter or longer may be employed in other embodiments, or changes in ECG axes may be determined substantially continuously on a rolling basis in still other embodiments.

The cardiac output module 150 receives information from the axis analysis module 140 (e.g., change information corresponding to a change in the difference between the QRS and T axes from a first time period to a second time period), and uses the information to determine a change in cardiac output. In some embodiments, the determined change in cardiac output is qualitative (e.g., cardiac output increasing or decreasing) and not necessarily quantitative. Generally speaking, in some embodiments, the cardiac output module 150 is configured to receive change information corresponding to changes in heart position based on changes in volume being pumped, to analyze the change information, and to track one or more trends to determine if the change in volume of the heart (and corresponding change in cardiac output) is increasing or decreasing.

For example, as discussed above, in some embodiments, if the change from the QRS axis to the T axis is increasing, then the cardiac output is understood as increasing. If the change from the QRS axis to the T axis is decreasing, then the cardiac output is understood as decreasing. As discussed above, the cardiac output may be defined as the product of the stroke volume and the heart rate. Thus, in some embodiments, the cardiac output module 150 may obtain heart rate information (e.g., as described by one or more R-R intervals) for the time periods, and factor any changes in heart rate into a determination of cardiac output. Thus, for example, an increase in difference between the QRS and T axes may be counteracted by a decrease in heart rate, or as another example, an increase in difference between the QRS and T axes may be augmented by an increase in heart rate in determining a change in cardiac output.

In still other embodiments, the correlation between changes of one or more axes (and/or one or more differences between two axes for a given cardiac cycle or group of cycles) and changes in cardiac output may be empirically determined. For example, ECG measurements of patients in clinical studies may be compared to measured cardiac output (for example, cardiac output measured by an invasive means, such as an arterial catheter). Then, changes in the ECG axes (or differences between axes) for the population of the clinical study may be compared to the measured cardiac outputs to determine which change or changes in ECG axes information best correlates to changes in cardiac output. The correlations determined may provide an equation or formula for converting changes in one or more axes over time to cardiac output, and/or may provide a lookup table correlating changes in one or more ECG axes to changes in cardiac output. The correlations may also be based in part on patient characteristics. For example, ECG axis orientations may be impacted by individual characteristics such as above normal levels of athletic training, enlarged heart, or previous heart attack resulting in portions of the heart that do not depolarize or depolarize substantially less than for a patient that did not have a previous heart attack. Thus, for example, different or modified formulas or lookup tables may be empirically determined and used for different population groups (e.g., a patient population with enlarged hearts). In some embodiments, a change in cardiac output may not be determined, or may not be provided, if certain cardiac arrhythmias are present that may substantially impair the accuracy of the determination.

Yet further still, the correlation between ECG axes and cardiac output may be individually determined for a given patient. For example, a patient may, upon initial admission, receive an arterial catheter that facilitates measurement of cardiac output. Then, changes in the ECG axes (or differences between axes) for the patient may be compared to the measured cardiac outputs to determine which change or changes in ECG axes information best correlates to changes in cardiac output, and, for example, to adjust or tailor a formula, equation, or look up table previously generated for a general population for the individual patient. As discussed above, the correlations determined may provide an equation or formula for converting changes in one or more axes over time to cardiac output, and/or may provide a lookup table correlating changes in one or more ECG axes to changes in cardiac output. Thus, at a later time, when an arterial catheter is no longer positioned within the patient, changes in one or more ECG axes may be used to determine changes in cardiac output for the patient.

In some embodiments, the cardiac output module 150 may be configured to provide an audible alarm, warning light, or other indication if a change in cardiac output exceeds a predetermined threshold or exhibits a rapid change. For example, the cardiac output module 150 may determine that the cardiac output has decreased a given amount or for a given amount of time, or as another example, may determine that cardiac output has decreased or remain unchanged after a treatment protocol configured to increase cardiac output. The cardiac output module 150, for example, in cooperation with a user interface module 160, may then provide a warning light, a readable message, or audible beep or other alarm indicating that a treatment protocol has been unsuccessful in increasing cardiac output and/or that additional treatment to increase cardiac output may be required.

The change in cardiac output determined by the cardiac output module 150 may include one or more of an absolute measurement (e.g., in Liters/minute), a trend (e.g., an indication that cardiac output is rising or falling, and, in some embodiments, a percentage corresponding to an amount the cardiac output is rising or falling), or a trend that tracks changes in cardiac output any may be calibrated based on absolute measurements taken from an additional measurement device (e.g., other than the detection module 110) associated with the patient.

The user interface module 160 is configured to receive user inputs and/or to display information to a user. For example, a user may change settings determining which axes are analyzed to determine changes in cardiac output, or may adjust time settings (e.g., the duration or number of samples taken and/or the interval between the times at which information samples are obtained) for obtaining ECG information. The user interface module 160 may include, or have associated therewith, a touch screen, a speaker, indicator light, keyboard, mouse, dials, or the like for displaying information and/or receiving user inputs.

The memory 170 is configured for use by one or more other aspects of the cardiac output monitor 120. Any suitable computer-readable media may be used in the system for data storage. Computer-readable media may be configured to store information that may be interpreted, for example, by a microprocessor. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

FIG. 6 illustrates an isometric view of an ECG monitoring system 600 according to an embodiment. In FIG. 6, the ECG monitoring system 600 is being used to monitor a patient 601. The ECG monitoring system 600 includes sensors 610a-j, an ECG monitor 632, and a multiparameter monitor 650. It should be noted that the placement of electrodes in FIG. 6 is intended by way of example, and specific positions of electrodes may vary. For example, the electrodes depicted on the arms may be positioned on the shoulders, and the electrodes depicted on the legs may be positioned slightly above the waist over the corresponding leg.

The sensors 610a-j in the illustrated embodiment are ECG electrodes attached to a patient. The sensors 610a-j are part of a 12-lead ECG detection system that may be included, for example, in a detection module such as detection module 110. The sensors 610a-j are configured as electrodes attached to an outer surface of the skin of the patient 601 and operably connected to a recording device such as the ECG monitor 632. For example, the electrodes may include a conducting gel embedded in an adhesive pad onto which cables connecting the electrodes to the ECG monitor 632 are attached.

The sensors 610a-j may be affixed to the patient as shown in the below table.

| Sensor | Placement |
|---|---|
| 610a | Right arm |
| 610b | Right leg |
| 610c | Left arm |
| 610d | Left leg |
| 610e | Fourth intercostal space (between ribs 4 & 5), to the right of the sternum |
| 610f | Fourth intercostal space (between ribs 4 & 5), to the left of the sternum |
| 610g | Between 610f and 610h |
| 610h | Fifth intercostal space (between ribs 5 & 6) in mid-clavicular line |
| 610i | Horizontally even with 610h in the left anterior axillar line |
| 610j | Horizontally event with 610i and 610j in midaxillary line |

In the illustrated embodiment the ten electrodes may be used in various combinations to define the 12 leads of a 12 lead system. For example, the sensors 610a-d are typically used in various combinations to define a frontal plane as used by the hexaxial reference system of FIGS. 3 and 4. Combinations additionally using the sensors 610e-j may be used to provide additional planes of axes for analysis.

The ECG monitor 632 includes a display 636 and a speaker 634. The ECG monitor 632 receives ECG information detected by the sensors 610a-j, and processes the information received from the sensors 610a-j. For example, the ECG monitor 632 may use the information to determine and display one or more ECG waveforms describing cardiac activity of the patient 601. The ECG monitor 632 may also determine various ECG axes using information obtained from the sensor 610a-j. In the illustrated embodiment, the ECG monitor 632 also includes, for example, a cardiac output analysis monitor 638. The cardiac output analysis monitor 638 may be similar to the previously described cardiac output monitor 120. In other embodiments, the cardiac output monitor 638 may be a free-standing unit, while in still other embodiments, the cardiac output monitor 638 may be incorporated into the multiparameter monitor 650. In embodiments where the cardiac output monitor 638 is freestanding, the cardiac output monitor 638 may receive ECG information directly from the sensors 610a-j, and/or may receive ECG information from the ECG monitor 632.

The multiparameter monitor 650 in the illustrated embodiment is configured to calculate physiological parameters and to provide a central display 652 for information from the ECG monitor 632 and from other medical monitoring devices or systems (not shown). For example, the multiparameter patient monitor 650 may also receive and/or display information from a pulse oximetry sensor, a blood pressure sensor, and/or other sensors or monitors. In some embodiments, the multiparameter monitor 650 may be connected to a network to enable the sharing of information (for example, cardiac output or ECG axis information) with servers or other workstations.

Figure 7:
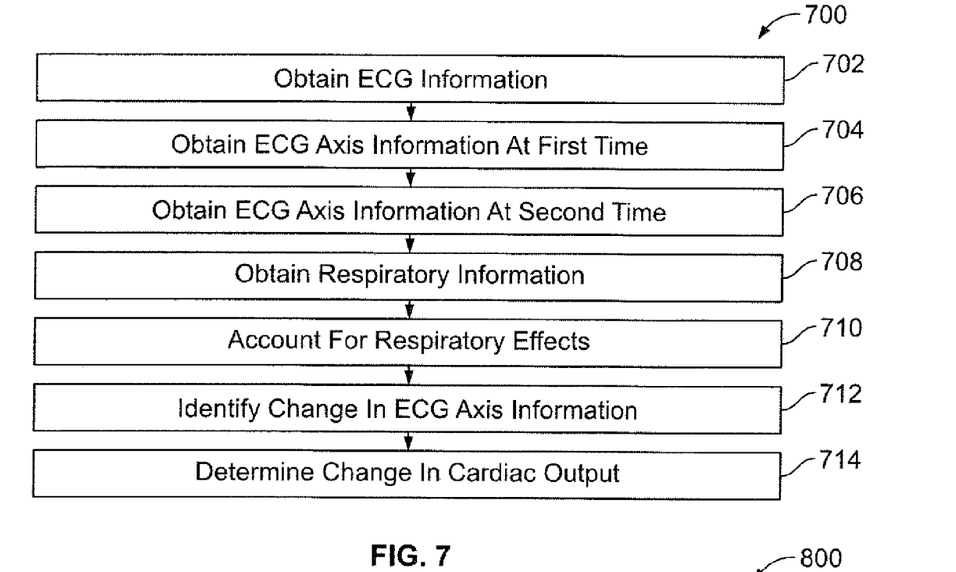
FIG. 7 illustrates a flowchart of a method for analyzing cardiac output according to an embodiment.

Certain embodiments provide a system and method for analyzing changes in cardiac output of a patient. For example, FIG. 7 provides a flowchart of a method 700 for analyzing cardiac output in accordance with various embodiments. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion. The method 700 may be performed, for example, in association with aspects, components, systems, and/or methods such as those discussed elsewhere herein.

At 702, ECG information is obtained. For example, ECG information may be obtained from a plurality of electrodes or other sensors or detectors affixed to or otherwise associated with a patient that measure electrical outputs corresponding to cardiac activity of the patient. The ECG information may be obtained, for example, by an input module 130 of a processing unit such as a cardiac output monitor 120. For example, in some embodiments, a four lead system may be employed. In other embodiments, other arrangements may be used. For example, in some embodiments, a 12 lead system (see e.g. FIG. 6 and related discussion) may be employed. Still other arrangements, such as a 15 lead system, or as another example, an 18 lead system may be employed in other embodiments. The ECG information may be provided as a group of ECG waveforms corresponding to cardiac activity of the patient as sensed by the plurality of electrodes. The ECG information may also include information describing or depicting the heart rate of the patient, such as, for example, an R-R interval.

At 704, ECG axis information is obtained at a first time. The ECG axis information may include information corresponding to one or more ECG axes for a given cardiac cycle, or may include information corresponding to one or more average ECG axes for a group of cycles. The ECG axis information may include information corresponding to a portion of the cardiac cycle, for example one or more of a p axis, a QRS axis, or a T axis. Additionally or alternatively, the ECG axis information may include axis difference information, for example a difference between a QRS axis and a T axis for a given cardiac cycle or group of cardiac cycles. For example, in some embodiments, ECG axis information is obtained for a given number of cardiac cycles, such as 15, or for a given time, such as about one minute. The ECG axis information may be obtained, for example, by an axis analysis module 140 or other aspect of a cardiac output monitor 120 that determines the orientation of one or more axes using ECG information, such as ECG waveforms, communicated from a sensing or detection module. In other embodiments, an axis analysis module 140 or other aspect of a cardiac output monitor 120 may obtain ECG axis information by receiving information describing or depicting ECG axes from a detection module or associated monitor. In some embodiments, the ECG axis information is obtained for one or more axes described in a frontal plane. In some embodiments, the ECG axis information is obtained for a different plane, or, as another example, for multiple planes (e.g. a three dimensional representation).

At 706, ECG axis information is obtained at a second time. The second time is temporally separated from the first time. For example, in some embodiments, the second time is about one hour after the first time. The type of ECG axis obtained at the second time may be substantially similar to the type of ECG axis information obtained at the first time. The ECG axis information may include information corresponding to a portion of the cardiac cycle, for example one or more of a p axis, a QRS axis, or a T axis, or, additionally or alternatively, the ECG axis information may include axis difference information, for example a difference between a QRS axis and a T axis for a given cardiac cycle or group of cardiac cycles. In some embodiments, the ECG axis information is obtained for a given number of cardiac cycles, such as 15, or for a given time, such as about one minute.

At 708, respiratory information is obtained. The respiratory information may be obtained, for example, from an analysis of ECG waveforms received by the axis analysis module 140 using conventional techniques. For example, using conventional techniques, ECG waveforms may be analyzed to determine the presence of respiratory cycles in the ECG waveforms. The respiratory information may include for example, information identifying the beginning and/or end of one or more respiratory cycles, information identifying the beginning and end of a given number of respiratory cycles, or information corresponding to a change in one or more ECG axes due to respiratory effects. In some embodiments, obtaining respiratory information may be omitted. For example, if ECG information is obtained and averaged over a sufficient amount of time, respiratory effects may effectively cancel or average each other out.

At 710, the respiratory information is accounted for by, for example, the axis analysis module 140. For example, in some embodiments, changes in the position or orientation of ECG axes due to respiration may be determined using conventional methods, and the ECG axis information obtained at the first and second times may then be adjusted to remove any changes in axis position or orientation due to respiration. In some embodiments, a sufficient number of cardiac cycles may be analyzed so that any respiratory effects are averaged out. For example, a predetermined integer number of respiratory cycles may be counted and ECG information collected for the predetermined integer number of respiratory cycles. For example, in some embodiments, first ECG axis information may be obtained for 15 respiratory cycles at the first time, and second ECG axis information may be obtained for 15 respiratory cycles at the second time, with first and second ECG axis information corresponding to average ECG axes for the first and second time periods, respectively. In other embodiments, a time period for obtaining ECG information is selected to be sufficiently long to allow respiratory effects to be averaged out. For example, in some embodiments, first ECG axis information may be obtained for about 60 seconds at the first time, and second ECG axis information may be obtained for about 60 seconds at the second time, with first and second ECG axis information corresponding to average ECG axes for the first and second time periods, respectively.

At 712, a change in ECG axis information is identified. For example, an axis analysis module 140 may generate ECG axis change information using the ECG axis information obtained at the first and second times. The ECG axis change information may correspond to a change in the orientation of one or more axes during a cardiac cycle (or group of cycles) at the first time and the orientation of corresponding one or more axes during a cardiac cycle (or group of cycles) at the second time. For example, the change information may correspond to a change in the orientation for the ECG axis corresponding to one or more of the p wave, Q wave, R wave, s wave, T wave, or QRS complex from the first time to the second time. The change information may, additionally or alternatively, correspond to one or more differences between axes of a cardiac cycle (or group of cycles). For example, the change information may correspond to a change in the difference between the QRS axis and the T axis from a first time to a second time.

At 714, a change in cardiac output is determined. For example, the change in cardiac output may describe whether cardiac output is increasing, decreasing, or remaining substantially the same from the first time period to the second time period. The change in cardiac output may be determined, for example, by a cardiac output module 150 or other aspect of a cardiac output monitor 120 that receives ECG axis change information from an axis analysis module (e.g., axis analysis module 140). For example, in some embodiments, the ECG axis change information includes information corresponding to a change in the difference between the QRS and T axes from a first time to the second time. When the difference between the QRS and T axes is increasing (with heart rate generally constant), the cardiac output may be understood as increasing; when the difference between the QRS and T axes is decreasing (with heart rate generally constant), the cardiac output may be understood as decreasing; and when the difference between the QRS and T axes is substantially unchanged (with heart rate generally constant), the cardiac output may be understood as substantially unchanged. In some embodiments, a cardiac output monitor may also obtain heart rate information and adjust the cardiac output determination accordingly to account for any change in heart rate from the first to the second time (for example, using the relationship CO=HR×SV discussed above). In other embodiments, correlations between one or more changes in axes and/or differences between axes of a given cycle (or groups of cycles) may be empirically determined, as discussed above. The empirical determination may be performed across a population of patients, and/or may be performed for an individual patient. For example, a formula correlating one or more changes in ECG axis information between a first time and a second time may be used to determine changes in cardiac output, or as another example, in some embodiments, the correlation may be included in a look up table accessible by the cardiac output module 150. Once the change in cardiac output is determined, an indication may be provided to a practitioner describing or otherwise relating to the change. For example, a warning light, message, or audible alarm may be provided if the change in cardiac output satisfies a predetermined condition or crosses a predetermined threshold. As another example, a message reading "cardiac output increasing," "cardiac output substantially unchanged," "cardiac output decreasing," or the like may be displayed on a screen.

Figure 8:
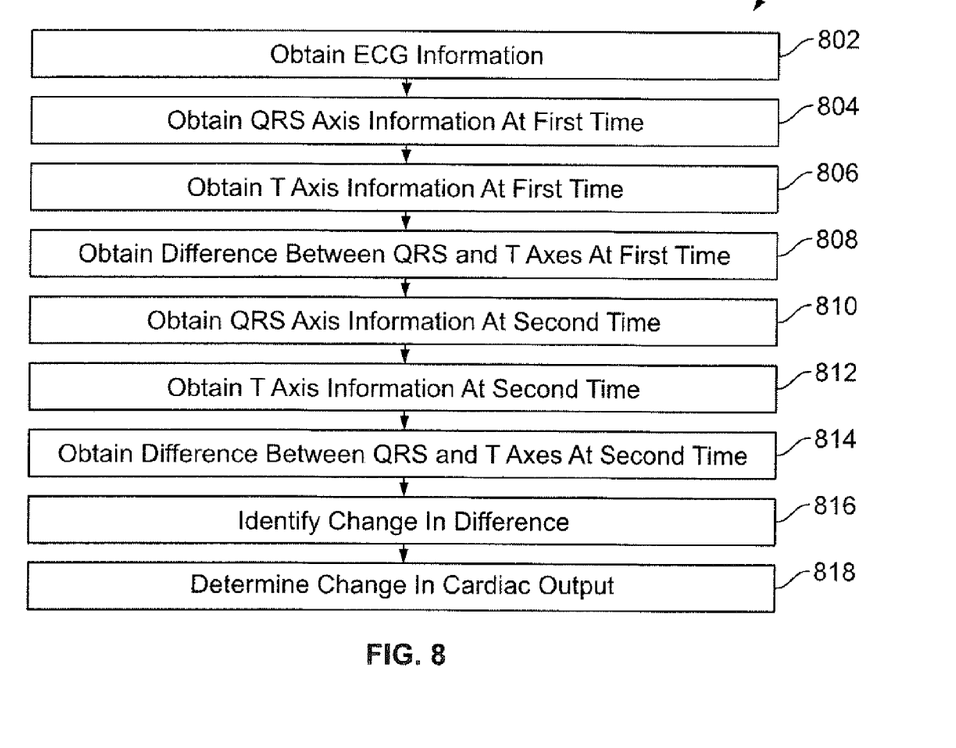
FIG. 8 illustrates a flowchart of a method for analyzing cardiac output according to an embodiment.

FIG. 8 illustrates a flowchart of a method 800 for analyzing changes in cardiac output in accordance with various embodiments. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion. The method 800 may be performed, for example, in association with aspects, components, systems, and/or methods such as those discussed elsewhere herein.

At 802, ECG information is obtained. As discussed above, for example, ECG information may be obtained from a plurality of electrodes or other sensors or detectors affixed to or otherwise associated with a patient that measure electrical outputs corresponding to cardiac activity of the patient. The ECG information may be obtained, for example, by an input module 130 of a processing unit such as a cardiac output monitor 120 from sensors or detectors that are included as part of a detection module 110. The ECG information, may be provided as a group of ECG waveforms corresponding to cardiac activity of the patient as sensed by the plurality of electrodes.

At 804, QRS axis information is obtained at a first time. For example, the QRS axis information may be obtained by an axis analysis module 140 that determines an average QRS axis orientation over a first time duration. For example, in some embodiments, the first time duration may be about 60 seconds. In some embodiments, the QRS axis orientation corresponds to an orientation in a frontal plane, while other planes or pluralities of planes may be employed in other embodiments.

At 806, T axis information is obtained at the first time. For example, the T axis information may be obtained by an axis analysis module 140 that determines an average T axis orientation over a first time duration. For example, in some embodiments, the first time duration may be about 60 seconds. Similar to the QRS axis information discussed in connection with 804, in some embodiments, the T axis orientation corresponds to an orientation in a frontal plane, while other planes or pluralities of planes may be employed in other embodiments.

At 808, the difference between the QRS axis information and the T axis information at the first time is obtained. As the QRS axis information corresponds to the depolarization and contraction of the ventricles, and the T axis information corresponds to the position of the heart during repolarization of the ventricles after blood has been pumped from the heart, the difference in the position of the axis between the QRS and T portions of the cardiac cycle may be understood as corresponding to the change in volume of the heart, and therefore corresponding to the stroke volume and cardiac output. For example, an axis analysis module 140 of a cardiac output monitor 120 may subtract the average T axis orientation obtained at 806 from the average QRS axis orientation obtained at 804. In other embodiments, for example, differences between other axes may be determined additionally or alternatively.

At 810, QRS axis information is obtained at a second time. The second time, for example, may be about one hour after the first time. In some embodiments, axis information may be obtained at more frequent intervals and/or changes may be tracked on a rolling basis. For example, similar to the QRS axis information for the first time period, the QRS axis information for the second time period may be obtained by an axis analysis module 140 that determines an average QRS axis orientation over the second time duration. In some embodiments, the second time duration may be about 60 seconds. In some embodiments, the QRS axis orientation corresponds to an orientation in a frontal plane, while other planes or pluralities of planes may be employed in other embodiments.

At 812, T axis information is obtained at the second time. Similar to the T axis information for the first time period, for example, the T axis information may be obtained by an axis analysis module 140 that determines an average T axis orientation over the second time duration. In some embodiments, the second time duration may be about 60 seconds. Similar to the QRS axis information discussed above, in some embodiments, the T axis orientation corresponds to an orientation in a frontal plane, while other planes or pluralities of planes may be employed in other embodiments.

At 814, the difference between the QRS axis information and the T axis information at the second time is obtained. For example, an axis analysis module 140 of a cardiac output monitor 120 may subtract the average T axis orientation obtained at 812 from the average QRS axis orientation obtained at 810.

At 816, a change in the difference between the QRS and T axes at the first and second times is obtained. For example, an axis analysis module 140 may determine change information describing the change in the difference between the QRS and T axes from the first to the second time.

At 818, a change in cardiac output is determined. For example, a cardiac output analysis module 150 may obtain change information from the axis analysis module 140 corresponding to the change in the difference between the QRS and T axes at the first and second times. In some embodiments, the cardiac output analysis module 150 may also obtain heart rate information corresponding to the heart rate of the patient at the first and second times. The cardiac output analysis module 150 may then use the heart rate information in conjunction with the change information to determine a change in cardiac output.

Thus, embodiments of the present disclosure provide for the non-invasive determination of cardiac output using readily available sensing components frequently attached to a patient for conventional monitoring techniques. Thus, embodiments of the present disclosure provide for cardiac output determination using relatively inexpensive and convenient detection techniques, as the expense and inconvenience of additional sensing or detecting equipment is avoided.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, FPGAs, logic circuits, and any other circuit or processor capable of executing the functions described herein. The above examples are exemplary only, and are thus not intended to limit in any way the definition and/or meaning of the term "computer."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. For example, a module or system may include a computer processor, controller, or other logic-based device that performs operations based on instructions stored on a tangible and non-transitory computer readable storage medium, such as a computer memory. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings without departing from its scope. While the dimensions, types of materials, and the like described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A system for analyzing cardiac output of a patient, the system comprising:
   a cardiac output monitor configured to be operatively connected to a detection module that obtains electrocardiogram (ECG) signals from the patient, the cardiac output monitor comprising:
      an axis analysis module configured to obtain ECG axis information, the ECG axis information comprising information corresponding to at least one ECG axis of the patient, the axis analysis module configured to determine ECG axis change information corresponding to a change in the ECG axis information of the patient; and
      a cardiac output analysis module configured to determine a change in cardiac output using the ECG axis change information.

2. The system of claim 1, wherein ECG axis information comprises first axis information corresponding to a first axis corresponding to a first portion of a cardiac cycle, second axis information corresponding to a second axis corresponding to a second portion of the cardiac cycle, and difference information corresponding to a computed value derived from the first axis information and the second axis information, and wherein the ECG axis change information comprises information describing a change in the difference information over time.

3. The system of claim 2, wherein the first axis corresponds to at least one of a Q wave, R wave, or S wave, and wherein the second axis corresponds to a T wave.

4. The system of claim 1, wherein the ECG axis information includes information corresponding to a multi-planar ECG axis.

5. The system of claim 1, wherein the cardiac output monitor is configured to adjust the ECG axis change information to account for a respiratory effect.

6. The system of claim 1, wherein the cardiac output monitor is configured to identify a predetermined number of breathing cycles, to collect a first set of the ECG axis information over a first group of breathing cycles, to collect a second set of the ECG axis information over a second group of breathing cycles, and to determine the ECG axis change information using a difference between the first set of the ECG axis information and the second set of the ECG axis information, wherein the first set and the second set of the ECG axis information are collected for the predetermined number of breathing cycles.

7. The system of claim 1, wherein the at least one ECG axis information comprises:
   first axis information corresponding to a first component of an ECG signal at a first time;
   second axis information corresponding to a second component of the ECG signal at the first time;
   third axis information corresponding to the first component of the ECG signal at a second time, wherein the second time differs from the first time; and
   fourth axis information corresponding to the second component of the ECG signal at the second time.

8. The system of claim 7, wherein the axis analysis module is configured to determine the ECG axis change information by obtaining a first difference between the first and second axis information, obtaining a second difference between the third and fourth axis information, and identifying a change between the first and second differences.

9. The system of claim 8, wherein the cardiac output analysis module is configured to determine the change in cardiac output by correlating changes in one or both of heart position or heart volume with the change between the first and second differences.

10. A method for analyzing changes in cardiac output of a patient, the method comprising:
    obtaining electrocardiogram (ECG) axis information of the patient, the ECG axis information based on information obtained from a detection module operatively connected to the patient;
    determining a change in the ECG axis information over time; and
    determining, at a processing unit, a change in cardiac output based on the change in the ECG axis information.

11. The method of claim 10, wherein the ECG axis information comprises first axis information corresponding to a first axis corresponding to a first portion of a cardiac cycle, second axis information corresponding to a second axis corresponding to a second portion of the cardiac cycle, and difference information corresponding to a computed value derived from the first axis information and the second axis information, and wherein the ECG axis change information comprises information describing a change in the difference information over time.

12. The method of claim 11, wherein the first axis corresponds to at least one of a Q wave, R wave, or S wave, and wherein the second axis corresponds to a T wave.

13. The method of claim 10, wherein the ECG axis information includes information corresponding to a multi-planar ECG axis.

14. The method of claim 10, further comprising adjusting the ECG axis change information to account for a respiratory effect.

15. The method of claim 14, wherein adjusting the ECG axis change information includes identifying a total change in the ECG axis information, identifying a portion of the total change attributable to respiration, and subtracting the portion attributable to respiration from the total change to obtain a net change in the ECG axis information.

16. The method of claim 10, further comprising identifying a predetermined number of breathing cycles, collecting a first set of the ECG axis information over a first group of breathing cycles, and collecting a second set of the ECG axis information over a second group of breathing cycles, wherein identifying the ECG axis change information comprises determining a difference between the first set of the ECG axis information and the second set of the ECG axis information, and wherein the first set and the second set of the ECG axis information are collected for the predetermined number of breathing cycles.

17. The method of claim 10, wherein the at least one ECG axis information comprises:
    first axis information corresponding to a first component of an ECG signal at a first time;
    second axis information corresponding to a second component of the ECG signal at the first time;
    third axis information corresponding to the first component of the ECG signal at a second time, wherein the second time differs from the first time; and
    fourth axis information corresponding to the second component of the ECG signal at the second time.

18. The method of claim 17, wherein the determining a change in the ECG axis information over time comprises:
    obtaining a first difference between the first and second axis information,
    obtaining a second difference between the third and fourth axis information, and
    identifying a change between the first and second differences.

19. The method of claim 18, wherein the determining, at a processing unit, a change in cardiac output based on the change in the ECG axis information comprises determining the change in cardiac output by correlating changes in one or both of heart position or heart volume with the change between the first and second differences.

20. A tangible and non-transitory computer readable medium comprising one or more computer software modules configured to direct a processor to:
    obtain electrocardiogram (ECG) axis information of a patient, the ECG axis information based on information obtained from a detection module operatively connected to the patient;
    determine a change in the ECG axis information over time; and
    determine a change in cardiac output based on the change in the ECG axis information.

21. The computer readable medium of claim 20, wherein the ECG axis information comprises first axis information corresponding to a first axis corresponding to a first portion of a cardiac cycle, second axis information corresponding to a second axis corresponding to a second portion of the cardiac cycle, and difference information corresponding to a computed value derived from the first axis information and the second axis information, and wherein the ECG axis change information comprises information describing a change in the difference information over time.

22. The computer readable medium of claim 21, wherein the first axis corresponds to at least one of a Q wave, R wave, or S wave, and wherein the second axis corresponds to a T wave.

23. The computer readable medium of claim 21, wherein the at least one ECG axis information comprises:
first axis information corresponding to a first component of an ECG signal at a first time;
second axis information corresponding to a second component of the ECG signal at the first time;
third axis information corresponding to the first component of the ECG signal at a second time, wherein the second time differs from the first time; and
fourth axis information corresponding to the second component of the ECG signal at the second time.

24. The computer readable medium of claim 23, wherein the computer readable medium is configured to direct the processor to determine the change in the ECG axis information over time by:
obtaining a first difference between the first and second axis information,
obtaining a second difference between the third and fourth axis information, and
identifying a change between the first and second differences.

25. The computer readable medium of claim 24, wherein the computer readable medium is configured to direct the processor to determine the change in the ECG axis information over time by correlating changes in one or both of heart position or heart volume with the change between the first and second differences.

26. The computer readable medium of claim 20, wherein the ECG axis information includes information corresponding to a multi-planar ECG axis.

27. The computer readable medium of claim 20, wherein the computer readable medium is further configured to adjust the ECG axis change information to account for a respiratory effect.

28. The computer readable medium in accordance of claim 27, wherein the computer readable medium is further configured to adjust the ECG axis change information by identifying a total change in the ECG axis information, identifying a portion of the total change attributable to respiration, and subtracting the portion attributable to respiration from the total change to obtain a net change in the ECG axis information.

29. The computer readable medium of claim 20, wherein the computer readable medium is further configured to direct the processor to identify a predetermined number of breathing cycles, collect a first set of the ECG axis information over a first group of breathing cycles, collect a second set of the ECG axis information over a second group of breathing cycles, and identify the ECG axis change information by determining a difference between the first set of the ECG axis information and the second set of the ECG axis information, wherein the first set and the second set of the ECG axis information are collected for the predetermined number of breathing cycles.

* * * * *